United States Patent [19]
Persson et al.

[11] Patent Number: 5,342,296
[45] Date of Patent: Aug. 30, 1994

[54] METHOD FOR DRAINING ANTRUM

[75] Inventors: Jan-Ove Persson, Havrevägen; Lars Lejdeborn, Västergöksvägen; Olle Berg, Elfviksvägen, all of Sweden

[73] Assignee: ATOS Medical AB, Horby, Sweden

[21] Appl. No.: 952,618

[22] Filed: Nov. 23, 1992

[30] Foreign Application Priority Data

May 23, 1990 [SE] Sweden .................. 9001857-3

[51] Int. Cl.⁵ .................................. A61M 31/00
[52] U.S. Cl. .................................. 604/49; 604/157; 606/108; 606/185
[58] Field of Search ............... 604/8, 49, 51, 54, 164, 604/157; 606/108, 109, 162, 99, 100, 184, 185; 128/753, 754

[56] References Cited

U.S. PATENT DOCUMENTS

| | | | |
|---|---|---|---|
| 2,699,784 | 1/1955 | Krayl | 606/185 |
| 2,725,878 | 12/1955 | Reiter | 606/100 |
| 3,888,258 | 6/1975 | Akiyama | 606/108 |
| 4,556,059 | 12/1985 | Adamson, Jr. | 604/157 |
| 4,737,141 | 4/1988 | Spits | 604/54 |
| 4,964,850 | 10/1990 | Bouton | 604/54 |
| 5,139,502 | 8/1992 | Berg et al. | 606/108 |
| 5,232,440 | 8/1993 | Wilk | 604/49 |

FOREIGN PATENT DOCUMENTS

| | | | |
|---|---|---|---|
| 0129634 | 1/1985 | European Pat. Off. | 606/108 |
| 0942729 | 7/1982 | U.S.S.R. | 606/108 |
| 8300429 | 2/1983 | World Int. Prop. O. | 604/51 |

Primary Examiner—John D. Yasko
Assistant Examiner—Anthony Gutowski
Attorney, Agent, or Firm—Joseph C. Mason, Jr.; Ronald E. Smith

[57] ABSTRACT

A method for inserting a drain catheter into an antrum includes the steps of securing a needle holder to the trailing end of a needle, positioning a hammer in predetermined spaced relation to the trailing end of the needle holder, loading a bias member so that it urges the hammer to strike the needle holder, restraining the hammer to maintain the load on the hammer, and quickly releasing the hammer and allowing it to strike the needle holder so that the leading end of the needle punctures the bone of the antrum wall. A first dampening member decelerates the hammer at the end of its displacement, and a second dampening member decelerates the needle and needle holder at the end of their joint displacement. A rigid tube is disposed in ensleeving relation to the needle so that the leading end of the tube is positioned in predetermined proximity to the point of the needle so that the leading end of the tube is carried into the antrum when the needle point punctures the antrum wall. A flexible catheter ensleeves a trailing end of the needle and a trailing end of the tube, and the catheter is bonded to the tube so that the tube and catheter remain together as a unit when the needle is withdrawn from the antrum. The tube and catheter provide a drain when the needle is withdrawn, the catheter having a trailing end that extends exteriorly of a patient's nose to facilitate drainage of the antrum.

8 Claims, 3 Drawing Sheets

METHOD FOR DRAINING ANTRUM

BACKGROUND OF THE INVENTION

1. Field of the Invention

This invention relates, generally, to medical appliances More particularly, it relates to a surgical tool and method for inserting a drain catheter into an antrum.

2. Description of the Prior Art

In the area of both human and veterinary medicine, it is normally desirable to get access to an antrum, for instance in inflammatory conditions when pus, blood or secretion is to be discharged or in other conditions when gases or liquids are to be evacuated. An example in human medicine is infection in the maxillarys sinus including pus therein, accumulation of blood or air in the thoracic cavity after trauma, urinary retention disabling depletion of the bladder, or conditions including accumulation of blood within or outside of the hard meninx. Also sampling from antrums are customary, for instance bone marrow sampling from medullary cavities.

Infection of maxillarys sinus including pus implies specific problems. As a result of swelling of the mucous membrane in the nose and maxillarys sinus at an upper respiratory infection, the normal outlets of the maxillarys sinus are closed. The air normally existing in said maxillarys sinus will be resorbed and the partial pressure decreases. Normally, already at this point the patient experiences a feeling of pressure in the affected maxillary sinus. If the process continues cilia action stops and mucous membrane secretion accumulates. In such an enviroment, the immunulogical defense against bacteria is deteriorated, and a bacterial infection with an accumulation of pus could arise. Because of the size and the anatomic structure with an outlet passage in a high position, the maxillary sinus is extremely subject to bacterial infections. There could also be a spreading of infections to the maxillary sinus from infected teeth of the upper jaw. The standard medical treatment comprises puncturing of the maxillary sinus by inserting a needle into the nasal cavity and engaging the wall of the maxillary sinus. Then the needle is forced through the bone wall into the maxillary sinus. In this way, material accumulated in the maxillary sinus can be sucked out for diagnosis, and then the maxillary sinus can be rinsed with a sodium chloride solution. However, it is difficult to puncture the maxillary sinus in this way. A careful anaesthesia is necessary and the doctor in charge has to be experienced. Even experienced otorhinolaryngologists may fail when performing the puncturing. A major cause of the problem is that the needle must be pressed through the bone at an oblique angle. A low space anatomy or a thick bone structure to the maxillary sinus in many cases inhibits a puncture. Thus the needle may slide in the mucous membrane and cause bleeding. Sometimes the maxillary sinus is reached only after applying a very hearty force on the needle and in such a case there is a risk that the needle will move forward through the rear wall of the maxillary sinus or into the eyeball; such complications are well documented. However, as the swelling of the mucous membrane, the closed outlet and a reduced transporting ability of the cilia will remain for a longer period of time (days or weeks), even if the treatment is favorable, it is nominally necessary to repeat the treatment several times before a complete healing of the infection is achieved. Each treatment requires a new puncture resulting in further discomfort to the patient and requiring comparatively large costs of treatment of a specialist. In practice this means that repeated antral washouts are performed only every second or every third day, even though from a medical point of view it would be more appropriate and lead to a faster healing if the antral washouts were made at least on a daily basis. Thus, it is desirable to decrease demands of repeated punctures in each case but to have a possibility of performing an antral washout as often as possible.

There have been attempts to decrease the number of repeated punctures, for instance by inserting a comparatively rigid catheter in the needle. When pressed into the maxillary sinus in a normal way the needle has been retracted. By a special shape of the catheter, either having the shape of a spiral or being provided with flanges, said catheter has been prevented from falling out of the maxillary sinus and it has been possible to perform antral washouts repeatedly without the necessity of repeated punctures. However, the methods have not become as popular as expected because none of the methods overcomes the difficulties and risks of forcing the needle into the maxillary sinus; instead a larger force is required to insert the needle and the catheter. Furthermore, use of the spiral preshaped catheter is unsafe and the catheter often comes out of the maxillary sinus. Both of said types of catheters are made of rigid plastics to facilitate the insertion which means that they are uncomfortable to the patients and cause problems and pain in the opening of the nose.

An object of the present invention is to overcome essentially the drawbacks and the problems mentioned above.

A further object of the invention is to make possible administration of medicines through the device.

BRIEF DESCRIPTION OF THE DRAWINGS

The invention will now be described in more detail by means of an embodiment, reference being made to the accompanying drawings, in which.

DETAILED DESCRIPTION OF THE PREFERRED EMBODIMENT

Figure 1:
FIG. 1 is a longitudinal sectional view of a device for draining the maxillary sinus according to the invention.

FIG. 1 shows that the maxillary sinus drain according to the invention comprises a hose or catheter 11 and a tube 12 connected thereto. Said catheter 11 is made of a soft and flexible material so as to extend, after applying said drain, through the nose without any major inconveniences to the patient and to be available from the opening of the nose. A suitable material for said catheter is rubber or thermoplastic elastomer preferably silicone rubber and vinyl chloride plastic. Said tube 12 is made of a rigid and hard material and is provided with thin walls so as to be inserted easily together with a needle through the wall of the maxillary sinus. Materials, such as metal, for example titanium or steel, or rigid plastic can be used in said tube 12. In a preferred embodiment, said tube and said catheter are fixedly connected to one another, preferably by gluing, and said catheter receiving a trailing end of said tube.

Figure 2:
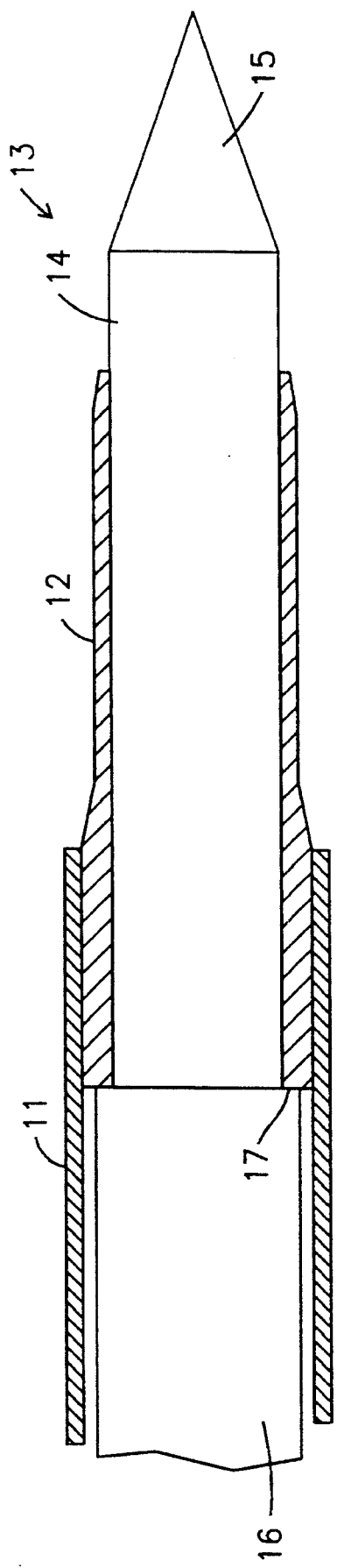
FIG. 2 is a longitudinal sectional view of a section of the drain of FIG. 1 in a larger scale and having a needle extending therethrough.

FIG. 2 shows a state in which said catheter 11 and said tube 12 have been threaded onto a needle 13, said needle comprising a needle point 15, a point section 14 having a first predetermined diameter and a base section 16 having a second predetermined diameter greater than the diameter of point section 14. An annular shoulder 17 is therefore formed between said point section 14 and said base section 16. Tube 12 engages said shoulder 17 when slide onto the needle 13 from the needlepoint end thereof. The leading end of said tube 12 is bevelled as at 12a to facilitate insertion of the said needle together with the catheter and tube through the bonewall between the nasal cavity and the maxillary sinus.

Figure 3:
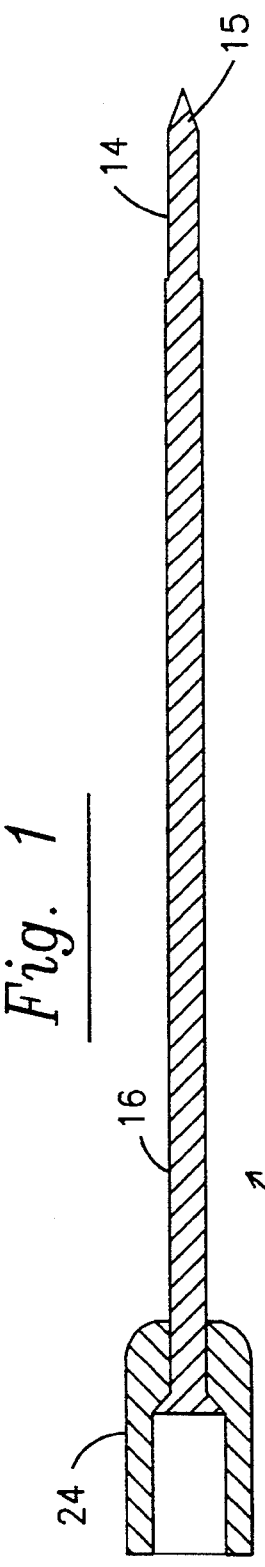
FIG. 3 is a sideview of the needle of FIG. 2.

FIG. 3 shows the entire needle 13. The trailing end of said needle comprises an internally threaded socket 24. Said socket is screwed together with the device described below before the drain is applied. In the preferred embodiment, said needle and said socket are made of a material facilitating a reuse after disinfection, such as steel, but it is also possible to provide the needle and socket as expendable products.

Figure 4:
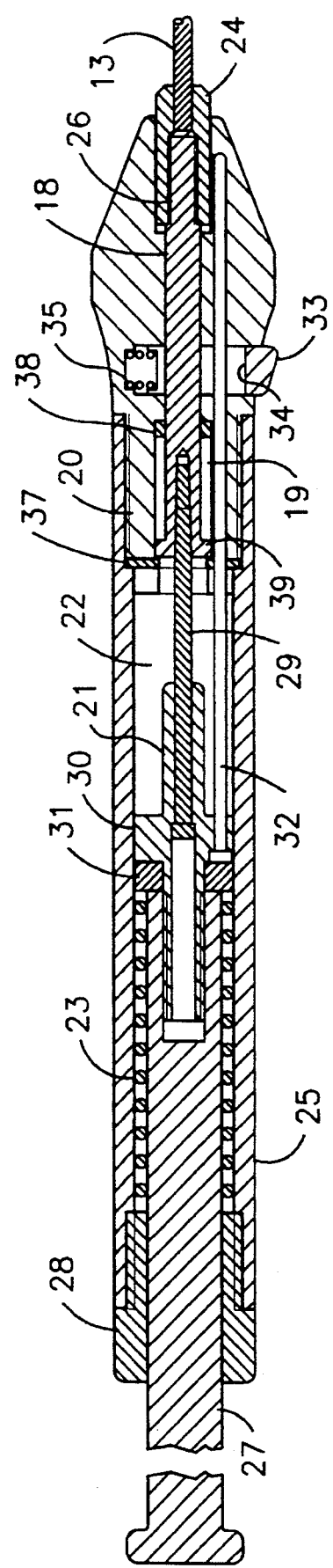
FIG. 4 is a longitudinal sectional view of a device for applying the drain according to FIGS. 1-3.

The invention is provided to overcomes problems during penetration of the bonewall into the maxillary sinus and the insertion of the drain therein. Said device is shown in FIG. 4 and comprises a cylindrical cover 25 having a head 20 and a trailing end section 28 enclosing several axially arranged hollow spaces. In a first hollow space 19 in said head 20 a needle holder 18 having a threaded leading end 26 and a needle 13 detachably connected to said needle holder 18 are arranged axially displaceable. Washer 37 abuts the trailing end of needle holder 18 and prevents its rearward motion. Forward travel of needle holder 18 is prevented by impact damper 38 which is also positioned in said first hollow space, said damper being engaged by an exterior flange 39 of said needle holder. Leading end 26 of said needle holder is threadedly connected to said socket 24, and a trailing end of said needle holder is threadedly connected to the leading end of return pin 29, a trailing end of said return pin being received within hammer 21.

Said hammer 21 is movably mounted in a second, elongated and axially extending hollow space 22, the leading end of space 22 being closed by annular damper 36. The trailing end of the return pin, received in said hammer, comprises an exterior flange engaging an interior shoulder of said hammer when said hammer is moved in the backward (leading-to-trailing) direction. Said hammer is connected by external threads formed in the trailing end thereof to a partly retractable cocking lever 27. Said cocking lever extends through said end section 28 which is screwed into the trailing end of said cylindrical cover 25. Said hammer is provided with an external flange 30. A stop washer 31 abuts the trailing said of said flange 30. Coil spring 23 is positioned between said stop washer 31 and said end section 28. Spring 23 is loaded, i.e., compressed, when cocking lever 27 is displaced in a leading-to-trailing direction, i.e, as indicated by the directional arrow at the left side of FIG. 4. Spacer 32 extends from said hammer to said head to lock said cocking lever 27 and hammer 21 in a state of tension. Said spacer 32 extends into an axial recess in said head and engages an elongated releasing pin 33 that is radially displaceable in a radial recess in said head. Said releasing pin 33 is formed with a first through opening extending in the transverse direction of said releasing pin, the needle holder 18 extending through said recess, and also a smaller recess 34 extending in the same direction through which releasing pin 33 moves when said releasing pin is disposed in a radially inward position in said radially extending recess. A spring 35 is provided in the bottom of said radially extending recess, said spring forcing said releasing pin outwardly towards an outer position in which said releasing pin is prevented from further movement in a trailing-to-leading direction.

Said hammer 21 is shaped cylindrically and is provided with a thin leading section, the outer diameter of said leading section being smaller than the inner diameter of said annular damper 36 and said washer 37. Therefor said hammer can extend through said damper 36 and said washer 37.

Figure 5:
FIG. 5 is a sideview of an alternative embodiment of the drain according to the invention.
Figure 6A:
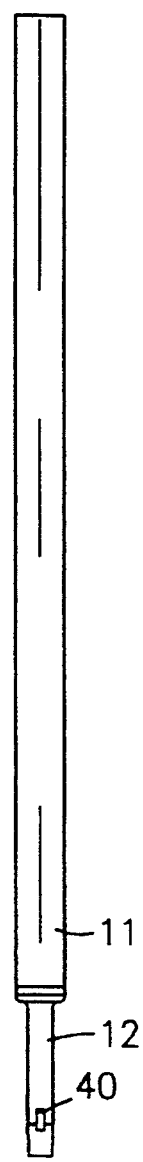
FIG. 6A is a front view of another embodiment of the drain according to the invention.
Figure 6B:
FIG. 6B is a sideview of the embodiment depicted in FIG. 6A.

FIGS. 5, 6A and 6B show two developments of said drain according to the invention. Said tube 12 is provided with elements to hamper an incidental retraction of the drain. Said tube 12 of said drain is according to FIG. 5 provided with barbs 41 in the free end thereof. The barbs are depicted in their unfolded configuration. Such an embodiment is intended first of all for use for patients having a bad wall to the maxillary sinus, for instance patients who have previously experienced medical surgery on said wall or patients whose wall has been punctured frequently in the conventional manner. The barbs are very thin, approximately 0.25 mm, and therefor they are folded during penetration and unfolded when retracted.

In the embodiment according to FIGS. 6A and 6B said tube 12 of the drain is provided with extending wedge shaped hooks 40, the narrower part thereof being disposed in the insertion direction of said tube.

The function of the device described above will now be described in more detail. Needle 13 is screwed into threaded leading end 26 of needle holder 18, and cocking lever 27 is pulled to load spring 23 and to move the return pin 29 and needle holder 18. When spacer 32, moving conjointly with hammer 21 has passed through recess 34 in releasing pin 33, said spring 35 urges said releasing pin into an upper position in which said spacer is barred from further movement in the forward (trailing-to-leading) direction. Now the device is in a ready state as shown in FIG. 4. The drain according to the invention is put onto needle 13, and the needle is inserted into the nose of a patient until the needlepoint engage the bone of the maxillary sinus. A suitable local anesthetic is previously administered in a suitable way, for example by an anesthetic spray. Releasing pin 33 is then depressed to allow spacer 32 to pass through recess 34 in a trailing-to-loading direction. Hammer 21 is accellerated by the force of spring 23 and moves sequentially through damper 36 and washer 37 and strikes the trailing end of needle holder 18, which together with said needle is pushed forwardly very rapidly. This causes the needle to penetrate the bone wall and causes the leading of the drain to pass through said bonewall. During the forward movement of hammer 21 return pin 29 is not directly affected by said hammer. The speed in the forward direction of needle holder 18 is reduced when the flange 39 of said needle holder engages impact damper 38 and when flange 30 of the hammer 21 engages damper 36. The length of stroke of said needle is determined by the distance between washer 37 and impact damper 38 and said distance is chosen from the anatomic conditions of the nose. The device including the needle is then removed from the nose while leaving said drain in position. Repeated washouts and tests can then be made without requiring further penetrations because the flexible catheter of the drain is easily available from the opening of the nose.

The excellent performance of the device is primarily attributable to the fast hammering action, the carefully calculated length of stroke, and the controlled deceleration of the needl. Other embodiments of the device performing the same function can be provided within the scope of the invention.

The releasing device may be varied in many ways within the scope of the invention. For example releasing elements from the arms industry may be employed. The stop 17 may be provided in the form of one or more radially extending pins or by a ring mounted in a groove. Other embodiments of a stop means for restricting axial displacement of the tube and catheter when put on the needle are also possible.

The drain according to the invention also has utility when administrating medicine or other substances to the antrum. To facilitate administration of medicine through the drain in different areas, said catheter in one embodiment is provided with a fixed adapter in the free end thereof, said adapter being intended for receiving a cannula or the like. In an alternative embodiment, the free end of said catheter is formed so as to be detachably connected to different types of adapters. The catheter is connected to syringes, dosage aggregates, suction devices or the like.

For specific types of medicine or during specific circumstances, it is appropriate to administer medicine into the antrum through a hose inserted through the catheter, said hose having a smaller diameter than said catheter. Such a method is appropriate especially when the medicine is intended for a certain part of the antrum.

For patients requiring continuous ventilation of an antrum, for instance the maxillary sinus, the drain according to the invention is provided with a shorted or an excluded catheter.

In the last described embodiment, the end of the tube opening into said antrum preferably is provided with an exterior flange to lower the risk that said tube unintentionally falls out. Also, when using the drain according to the first described method it is under certain circumstances appropriate to provide said tube with such a flange.

We claim:

1. A method for inserting a drainage means into an antrum, comprising the steps of:
   securing the trailing end of a needle having a drainge means in a needle holder;
   slidably mounting said needle holder so that it can slide along its longitudinal axis of symmetry between a retracted position and an extended position, the distance between said retracted and extended positions being the operating travel range of said needle holder and hence of said needle;
   positioning a hammer means in spaced apart relation to a trailing end of the needle holder when the needle holder is in its retracted position;
   positioning a bias means in trailing relation to the hammer means and loading said bias means so that it urges said hammer means to strike said needle holder;
   restraining said bias means; and
   abruptly releasing said bias means so that said bias means drives said hammer means into striking engagement with said needle holder and hence said needle;
   said needle holder being abruptly displaced from its retracted position to its extended position upon being struck by said hammer means;
   whereby the operating travel range of said needle holder determines the length of travel of said needle and thus the depth of penetration of said needle and drainge means into said antrum when said needle holder is struck.

2. The method of claim 1, further comprising the steps of:
   ensleeving a predetermined extent of the needle in a rigid tube; and
   positioning a leading end of said rigid tube in predetermined proximity to the leading end of the needle so that at least a predetermined leading extent of the tube is introduced into the antrum when the needle enters into the antrum so that the tube may serve as a drain means when the needle is withdrawn therefrom.

3. The method of claim 2, further comprising the step of:
   preventing leading-to-trailing displacement of said tube with respect to the needle by forming a radially outwardly extending shoulder means in the needle at the trailing end of the tube.

4. The method of claim 3, further comprising the step of:
   bonding an elongate flexible catheter to a trailing end of the tube so that the trailing end of the catheter extends externally of a patient's nose when the leading end of the tube is positioned within the antrum.

5. The method of claim 1, further comprising the steps of:
   cushioning the deceleration of the needle holder and needle after the needle point has entered the antrum;
   cushioning the deceleration of the hammer means after the hammer means has struck the trailing end of the needle holder;
   whereby the rate of deceleration of both the hammer and needle are controlled.

6. The method of claim 1, further comprising the step of:
   controlling the extent of the travel of the needle holder and needle by positioning means for stopping travel of needle holder and hammer means in predetermined relation to one another.

7. A method for inserting a drainage means into an antrum, comprising the steps of:
   providing an elongate needle having a pointed leading end for puncturing bone matter;
   ensleeving a predetermined extent of said needle in a rigid tube;
   supporting a trailing end of said tube so that said tube may not move along the extent of said needle in a leading-to-trailing direction;
   positioning a leading end of said tube in predetermined trailing relation to said point of said needle so that when said point of said needle punctures said bone, thereby creating a puncture opening in said bone, a leading end of said tube is carried through said puncture opening with said needle;

positioning a hammer means in trailing relation to said needle and biasing said hammer means in a trailing-to-leading direction;

abruptly unloading said bias means so that it strikes the trailing end of said needle and drives said needle through said bone matter; and retracting said needle from said tube after said puncture opening has been formed;

whereby said leading end of said tube remains inserted into said antrum through said puncture opening so that liquid fluid contained in said antrum may drain therefrom through said tube.

8. The method of claim 7, further comprising the steps of ensleeving a trailing end of said tube within a leading end of an elongate catheter, and bonding said tube and elongate catheter to one another so that a trailing end of said elongate catheter is positioned externally of a patient's nose when the method steps have been completed.

* * * * *